United States Patent [19]
Rohr et al.

[11] 4,376,646
[45] Mar. 15, 1983

[54] HERBICIDAL N-[4-(3'-ALKOXYPHENOXY)-PHENYL]-N'-METHYLUREAS

[75] Inventors: Otto Rohr, Therwil, Switzerland; Georg Pissiotas, Lörrach, Fed. Rep. of Germany

[73] Assignee: Ciba-Geigy Corporation, Ardsley, N.Y.

[21] Appl. No.: 241,295

[22] Filed: Mar. 6, 1981

[30] Foreign Application Priority Data

Mar. 18, 1980 [CH] Switzerland .......................... 2123/80
Mar. 18, 1980 [CH] Switzerland .......................... 2124/80

[51] Int. Cl.³ .................. A01N 9/20; C07C 127/19
[52] U.S. Cl. ........................................... 71/120; 71/88; 71/90; 71/92; 71/94; 71/95; 71/98; 71/103; 71/105; 71/106; 260/453 RW; 260/456 A; 260/465 D; 560/251; 564/49; 564/51; 564/52
[58] Field of Search .............. 564/49, 51, 52; 71/120; 260/465 D, 456 A, 453 RW; 560/251

[56] References Cited

U.S. PATENT DOCUMENTS

| | | | |
|---|---|---|---|
| 3,060,235 | 10/1962 | Martin et al. .................. | 71/120 X |
| 3,707,557 | 12/1972 | Brown .............................. | 71/120 X |
| 3,819,697 | 6/1974 | Cross ................................ | 71/120 X |
| 3,933,814 | 1/1976 | Haberkorn et al. ............. | 564/49 X |
| 4,080,193 | 3/1978 | Rohe et al. ...................... | 71/120 |
| 4,087,272 | 5/1978 | Rohe et al. ...................... | 71/120 |
| 4,249,938 | 2/1981 | Takemoto et al. .............. | 71/120 X |
| 4,260,411 | 4/1981 | Yoshida et al. .................. | 71/120 X |
| 4,279,637 | 7/1981 | Wu .................................... | 564/52 X |

Primary Examiner—Thomas A. Waltz
Attorney, Agent, or Firm—Frederick H. Rabin

[57] ABSTRACT

Novel ureas of the formula I have herbicidal activity and are suitable in small applied amounts for selectively combating weeds in cultivated crops of soya-bean, maize and cereals. They are advantageously produced by the isocyanate method and correspond to the formula I

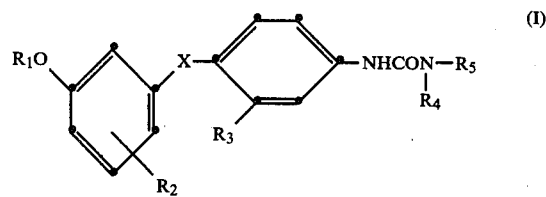

wherein
$R_1$ is an unsubstituted or substituted $C_1$–$C_6$-alkyl, $C_2$–$C_6$-alkenyl, $C_2$–$C_6$-alkynyl, aralkyl, phenyl, acyl or $C_1$–$C_4$-alkylsulfonyl group or an aminoalkyl group,
$R_2$ is hydrogen, halogen, $C_1$–$C_4$-alkyl or $C_1$–$C_4$-alkoxy,
$R_3$ is hydrogen, halogen, cyano or trifluoromethyl,
$R_4$ is hydrogen, $C_1$–$C_6$-alkyl, $C_2$–$C_6$-alkenyl, $C_2$–$C_6$-alkynyl or $C_1$–$C_6$-alkoxy,
$R_5$ is hydrogen, $C_1$–$C_6$-alkyl or $C_2$–$C_6$-alkenyl, or $R_5$ together with $R_4$ and the nitrogen atom to which they are bound also form a 5-6-membered heterocycle, and
X is oxygen, sulfur or the sulfinyl or sulfonyl group.

17 Claims, No Drawings

HERBICIDAL N-[4-(3'-ALKOXYPHENOXY)-PHENYL]-N'-METHYLUREAS

The present invention relates to novel ureas having herbicidal activity, to their production, to compositions containing them, and to their use for selectively combating weeds in various cultivated crops.

It is known from many patent applications that diphenyl ethers and phenylureas are excellent herbicides, for example U.S. Pat. Nos. 2,655,445, 2,655,447, 3,080,225, and others.

The combination of diphenyl ether and urea is likewise known, for example from the German Offenlegungsschrift No. 2,411,320, the Belgian Pat. No. 623,440 and the Swiss Pat. Nos. 384,282, 493,195 and 503,459. It has now been found that the novel derivatives of the present invention surprisingly have a good ratio of activity to selectivity, this applying in particular in the case of a post-emergence application for example in crops of soya-bean, maize and cereals.

The novel compounds correspond to the formula I

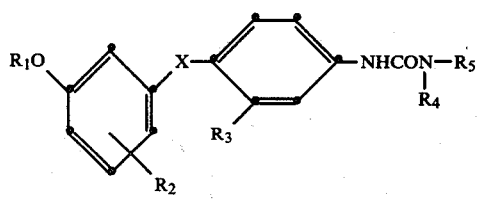

wherein $R_1$ is a $C_1$–$C_6$-alkyl, $C_2$–$C_6$-alkenyl, $C_2$–$C_6$-alkynyl, aralkyl, phenyl, $C_1$–$C_6$-haloalkyl, $C_1$–$C_6$-cyanoalkyl, $C_2$–$C_6$-alkoxyalkyl, $C_2$–$C_6$-alkylthioalkyl, acyl, haloacyl or $C_1$–$C_4$-alkylsulfonyl group, or a group

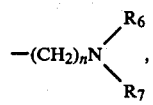

$R_2$ is hydrogen, halogen, $C_1$–$C_4$-alkyl or $C_1$–$C_4$-alkoxy, $R_3$ is hydrogen, halogen, cyano or trifluoromethyl, $R_4$ is hydrogen, $C_1$–$C_6$-alkyl, $C_2$–$C_6$-alkenyl, $C_2$–$C_6$-alkynyl or $C_1$–$C_6$-alkoxy, $R_5$ is hydrogen, $C_1$–$C_6$-alkyl or $C_2$–$C_6$-alkenyl, or $R_5$ together with $R_4$ and the nitrogen atom to which they are bound also form a 5-6-membered heterocycle, $R_6$ and $R_7$ are each separately hydrogen, $C_1$–$C_6$-alkyl or $C_2$–$C_6$-alkenyl, or together with a nitrogen atom to which they are bound they also form a 5-6-membered heterocycle, n is a number 1, 2 or 3, and X is oxygen, sulfur or the sulfinyl or sulfonyl group.

In the above definitions, "alkyl" can be any straight-chain or branched-chain alkyl group having up to 6 carbon atoms. Alkenyl and alkynyl groups have 2 to 6 carbon atoms, can be straight-chain or branched-chain and can have one or two unsaturated positions. Aralkyl groups are phenyl groups which are bound by a straight-chain or branched-chain $C_1$–$C_6$-alkylene chain to the molecule. Phenyl groups can be unsubstituted or mono- or polysubstituted by halogen, $C_1$–$C_4$-alkyl, $C_1$–$C_4$-alkoxy, $C_1$–$C_4$-alkylthio, cyano, nitro or trifluoromethyl. Acyl groups $R_1$ are radicals of alkanecarboxylic acids, which are bound by way of the ester function to the oxygen atom; or radicals of hydroxycarboxylic acids, which are bound by way of the hydroxyl group, and esters thereof, for example hydroxyacetic acid, α- or β-hydroxypropionic acids as well as α-, β- or γ-hydroxybutyric acids. Haloacyl groups are halogenated alkanecarboxylic acids and esters thereof, for example chloroacetic acid. The 5-6-membered heterocycles, which can be formed by the radicals $R_4$ and $R_5$ and $R_6$ and $R_7$, respectively, together with the nitrogen atom to which they are bound, are pyrrolidine, piperidine, morpholine, thiomorpholine or piperazine rings. These can be substituted by methyl, and the piperazine ring also by phenyl. By halogen is meant fluorine, chlorine, bromine and iodine, with chlorine being preferred.

The compounds of the formula I are produced by a known procedure suitable for ureas.

The process for producing the ureas of the formula I comprises reacting an isocyanate of the formula II

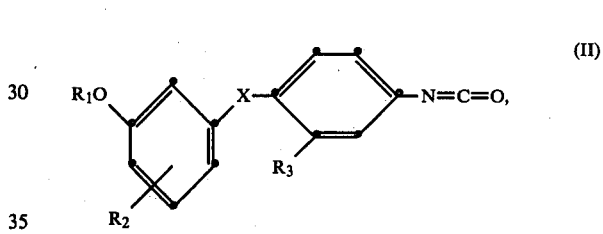

wherein $R_1$, $R_2$ and $R_3$ have the meanings defined in the foregoing, in an inert organic solvent or diluent, with an amine of the formula III

wherein $R_4$ and $R_5$ have the meanings defined in the foregoing.

This reaction can be performed at 0°–150° C., that is to say, it can be performed quite well at room temperature. The temperature is generally briefly raised to the boiling point for the purpose of shortening the reaction time.

Suitable solvents or diluents for this reaction are organic solvents miscible with water, for example acetone, acetonitrile, higher ketones, dimethylformamide, dimethylsulfoxide, dioxane, and so forth. The reaction is in general performed under normal pressure, but larger amounts can be produced also in pressure vessels.

The starting materials of the formula II in which X is oxygen are produced for example by the following reaction sequence: a phenol of the formula IV is reacted with a halogenonitrobenzene of the formula V, in the course of which a para-nitrodiphenyl ether of the formula VI is formed; this is then reduced to the corresponding para-diphenyl ether amine of the formula VII, which in its turn is converted, for example by means of phosgene, to the isocyanate of the formula II

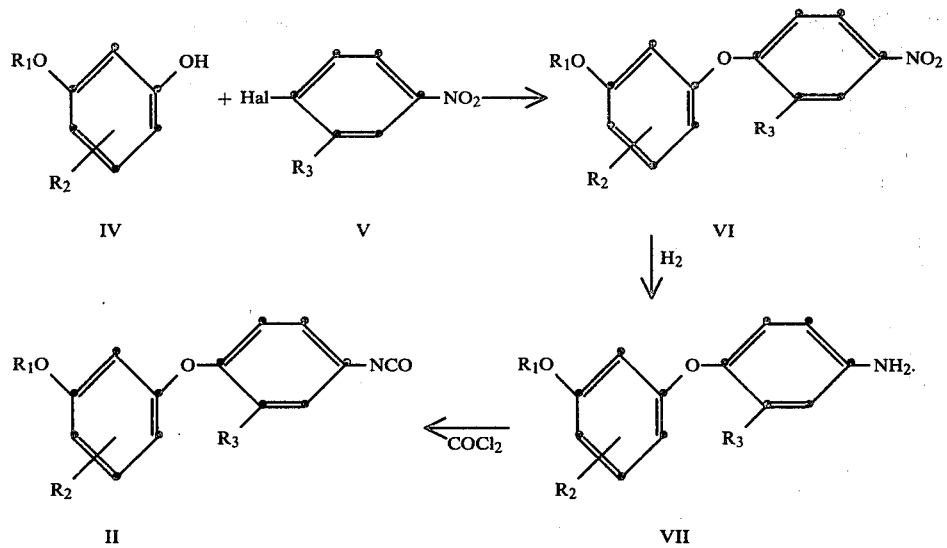

In the formulae II to VII, the symbols $R_1$ and $R_2$ have the meanings defined in the foregoing, and "Hal" is halogen. Individual nitrodiphenyl ethers of the formula VI are described in the Japanese Published Specification No. 73432/66. Other starting materials of the formula II can be produced in an analogous manner.

The compounds of the formula I have marked selective-herbicidal properties in general, and prove to be particularly advantageous for combating weeds in crops of productive plants, especially crops of soya-bean, cereals and maize. Where the amount applied is sufficiently great, however, there also results a total herbicidal action. The application can be carried out both in the pre-emergence process and in the post-emergence process. The amounts applied can vary within wide limits, for example between 0.1 and 10 kg of active substance per hectare; preferably however the amount applied is between 0.5 and 5 kg of active substance per hectare.

The compounds of the formula I are suitable in particular for post-emergence application as selective herbicides in crops of soya-bean, rice and cereals. In a comparison of the action of compounds according to the invention and that of known herbicides in the above-mentioned crops, the action of the compound No. 1 surpassed that of the commercial products with regard to selectivity and activity in the wheat and soya-bean crops; the compound No. 39 was better in wheat crops and the compound No. 45 in rice crops. Also the other compounds according to the invention excel by virtue of their extremely favourable activity/selectivity ratio.

A particularly good action is exhibited by the ureas of the formula Ia

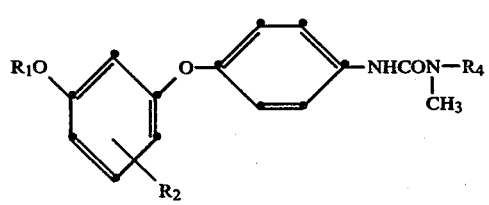

(Ia)

wherein $R_1$ is a straight-chain or branched-chain $C_1$–$C_6$-alkyl group, $R_2$ is hydrogen, halogen, methyl or methoxy, and $R_4$ is methyl or methoxy;

the best action of all however is exhibited by those compounds in which $R_2$ is hydrogen.

The compounds of the formula I are stable compounds. They are negligibly toxic to warm-blooded animals, and their handling requires no precautionary measures. They have relatively high solubility in the customary organic solvents and low solubility in water. They can be easily precipitated by the addition of water to the reaction solution. Their formulation as liquid herbicidal compositions is possible only with the aid of special solubility-promoting agents and/or dispersing agents.

Compositions according to the invention contain, in addition to the active substance of the formula I, a suitable carrier and/or other additives. Suitable carriers and additives can be solid or liquid and they correspond to the substances customarily used in formulation practice.

The compositions according to the invention are produced in a manner known per se by the intimate mixing and grinding of active substances of the general formula I with suitable carriers and/or distributing agents, optionally with the addition of antifoaming agents, wetting agents, dispersing agents and/or solvents, all inert to the active substances. The active substances can be obtained and used in the following forms:

solid preparations: dusts, scattering agents, granulates (coated granules, impregnated granules and homogeneous granules);

water-dispersible concentrates of active substance: wettable powders, pastes, emulsions and emulsion concentrates, and liquid preparations: solutions.

The concentration of active substance in the compositions according to the invention is 1 to 80 percent by weight, and when being applied the compositions can if necessary contain the active substance also at a lower concentration, such as about 0.05 to 1 percent by weight.

Other biocidal active substances or compositions can be mixed with the compositions according to the invention. For broadening their scope of action, the novel compositions can thus contain, besides the stated compounds of the general formula I, for example insecticides, fungicides, bactericides, fungistatics, bacteriostatics or nematocides, or further herbicides.

The examples which follow are intended to further illustrate the production of the diphenyl ether ureas of the formula according to the invention. Other compounds produced in an analogous manner are listed in the Table following Example 2. The temperatures are given in degrees Centigrade; parts and percentages are by weight, and pressure values are expressed in millibars. The processing of the active substances into commercially usable preparations, and also tests to demonstrate the herbicidal activity are described in subsequent Examples.

EXAMPLE 1

N-[4-(3'-methoxyphenoxy)-phenyl]-N'-methoxy-N'-methylurea

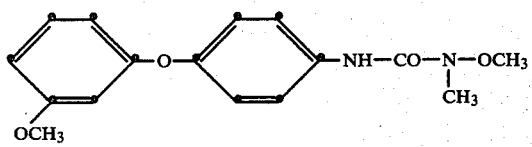

(a) 124.1 g (1 mol) of 3-methoxyphenyl and 44 g (1.1 mols) of powdered sodium hydroxide are placed into 700 ml of dimethyl sulfoxide. There are then added dropwise 157.5 g of p-chloronitrobenzene dissolved in 100 ml of dimethylsulfoxide, and the mixture is heated overnight at 120°. The reaction product thus obtained is poured into ice/water and filtered off. The filtrate is washed with water and dried in a drying chamber at 50°. The yield is 231 g of 4-nitro-3'-methoxydiphenyl ether, m.p. 82°–85°.

(b) 98 g (0.4 mol) of 4-nitro-3'-methoxydiphenyl ether are dissolved in ethanol and, after the addition of Raney nickel, the solution is hydrogenated. After completion of hydrogen absorption, the catalyst is filtered off and the solvent is distilled off. The oil thus obtained is distilled in vacuo and has a boiling point of 143° at 0.04 millibar.

(c) 25 g of phosgene are introduced at about −20° into 250 ml of ethyl acetate. At the same temperature, there are then added dropwise 43 g (0.2 mol) of the amine obtained under (b), which has been dissolved beforehand in 100 ml of ethyl acetate. The mixture thus obtained is heated, with the simultaneous introduction of phosgene, in the course of one hour to 70°. The reaction mixture is stirred at this temperature for a further half hour and subsequently cooled to room temperature, and for 30 minutes nitrogen instead of phosgene is passed through the solution. After the solvent has been distilled off, the isocyanate thus obtained is further processed in the crude state.

(d) 18.3 g (0.3 mol) of methoxymethylamine are dissolved in 100 ml of acetonitrile. There is subsequently added dropwise, with thorough stirring, a solution of 0.1 mol of the above isocyanate in 50 ml of acetonitrile. The reaction mixture is stirred for a further 30 minutes and then poured into ice/water. The aqueous mixture is extracted with ethyl acetate/toluene (1:1). The organic phase is dried over sodium sulfate, and the solvent is afterwards evaporated off. The yield is 30 g of the title compound as viscous oil having a refractive index of $n_D^{29} = 1.5707$.

Analysis: Calculated: C, 63.57; H, 6.00; N, 9.27%. Found: C, 64.30; H, 6.10; N, 8.90%.

EXAMPLE 2

N-[4-(3'-α-propionitriloxy-phenoxy)-phenyl]-N',N'-dimethylurea

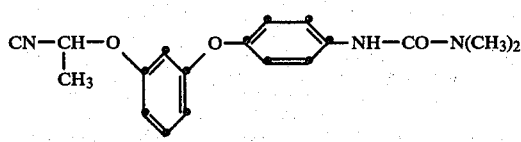

(a) 23.1 g of 4-nitro-3'-hydroxydiphenyl ether and 15 g of bromopropionic acid nitrile in ethyl-methyl ketone, in the presence of the threefold amount of potassium carbonate, are stirred overnight at 80°. The reaction product is filtered off and concentrated by evaporation to yield 28 g of oil: 4-nitro-3'-(α-propionitriloxy)-diphenyl ether.

(b) The diphenyl ether obtained under (a) is hydrogenated according to Bechamp (with iron filings and concentrated hydrochloric acid), and the crude 4-phenoxyaniline is isolated and subsequently reacted with phosgene to the corresponding isocyanate.

0.05 mol of the isocyanate thus obtained is dissolved in 50 ml of acetonitrile, and slowly added dropwise to a solution of 6 g of dimethylamine in 100 ml of acetonitrile. After the reaction has finished, water is added and the crystals which precipitate are filtered off. The yield after drying in vacuo is 10.6 g of the title compound in the form of white powder, m.p. 105°–111° (compound No. 25).

The following compounds are produced in an analogous manner:

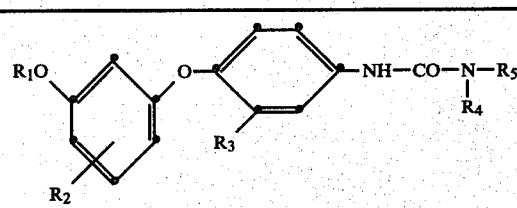

| No. | R₁O— | R₂ | R₃ | R₄ | R₅ | Phys. data |
|-----|------|-----|-----|------|------|------------|
| 1 | CH₃O | — | — | OCH₃ | CH₃ | $n_D^{29}$ 1.5707 |
| 2 | CH₃O | — | — | CH₃ | CH₃ | m.p. 139–141° |
| 3 | CH₃O | 6-Cl | — | CH₃ | CH₃ | m.p. 141–143° |
| 4 | CH₃O | 6-Cl | — | OCH₃ | CH₃ | m.p. 96–97° |

-continued

| No. | R₁O | R₂ | R₃ | R₄ | R₅ | Phys. data |
|---|---|---|---|---|---|---|
| 5 | CH₃O | 5-OCH₃ | — | CH₃ | CH₃ | m.p. 140–141° |
| 6 | CH₃O | 5-OCH₃ | — | OCH₃ | CH₃ | m.p. 99–100° |
| 7 | CH₃O | 4-Cl | — | CH₃ | CH₃ | m.p. 139–140° |
| 8 | CH₃O | 4-Cl | — | OCH₃ | CH₃ | m.p. 93–94° |
| 9 | C₂H₅O | — | — | OCH₃ | CH₃ | oil |
| 10 | C₂H₅O | — | — | CH₃ | CH₃ | m.p. 121–128° |
| 11 | C₂H₅O | 6-Cl | — | CH₃ | CH₃ | |
| 12 | C₂H₅O | 6-Cl | — | OCH₃ | CH₃ | |
| 13 | C₂H₅O | 4-Br | — | CH₃ | CH₃ | |
| 14 | C₂H₅O | 4-Br | — | OCH₃ | CH₃ | |
| 15 | C₂H₅O | 4-Cl | — | CH₃ | CH₃ | |
| 16 | C₂H₅O | 4-Cl | — | OCH₃ | CH₃ | |
| 17 | OC₃H₇ iso | — | — | CH₃ | CH₃ | m.p. 92–96° |
| 18 | OC₃H₇ iso | — | — | OCH₃ | CH₃ | $n_D^{26}$ 1.5692 |
| 19 | OC₃H₇ iso | 6-Cl | — | CH₃ | CH₃ | |
| 20 | OC₃H₇ iso | 6-Cl | — | OCH₃ | CH₃ | |
| 21 | OC₃H₇ iso | 4-Br | — | CH₃ | CH₃ | |
| 22 | OC₃H₇ iso | 4-Br | — | OCH₃ | CH₃ | |
| 23 | OC₃H₇ iso | 4-Cl | — | CH₃ | CH₃ | |
| 24 | OC₃H₇ iso | 4-Cl | — | OCH₃ | CH₃ | |
| 25 | OCH(CH₃)CN | — | — | CH₃ | CH₃ | m.p. 105–111° |

| No. | R₁O | R₂ | R₃ | R₄ | R₅ | Phys. data |
|---|---|---|---|---|---|---|
| 26 | OCH(CH₃)CN | — | — | OCH₃ | CH₃ | oil |
| 27 | OCH₂—(furyl) | — | — | CH₃ | CH₃ | m.p. 85–87° |
| 28 | OCH₂—(furyl) | — | — | OCH₃ | CH₃ | m.p. 95–96° |
| 29 | OCOCH₃ | — | — | CH₃ | CH₃ | m.p. 137–139° |
| 30 | OCOCH₃ | — | — | OCH₃ | CH₃ | oil |
| 31 | OCH₃ | | | | | |
| 32 | OCH(CH₃)CN | 4-Cl | — | CH₃ | CH₃ | m.p. 146–148° |
| 33 | OCH(CH₃)CN | 4-Cl | — | OCH₃ | CH₃ | m.p. 118–119° |
| 34 | OCH(C₂H₅)CN | 4-Cl | — | CH₃ | CH₃ | m.p. 104–110° |
| 35 | OCH(C₂H₅)CN | 4-Cl | — | OCH₃ | CH₃ | oil |
| 36 | OCH(CH₃)CN | 6-Cl | — | CH₃ | CH₃ | m.p. 125–128° |
| 37 | OCH(CH₃)CN | 6-Cl | — | OCH₃ | CH₃ | oil |
| 38 | OCH₃ | — | Cl | CH₃ | CH₃ | m.p. 168–170° |
| 39 | OCH₃ | — | Cl | OCH₃ | CH₃ | $n_D^{26}$ 1.5843 |
| 40 | OCH(CH₃)CN | — | Cl | CH₃ | CH₃ | m.p. 80–84° |
| 41 | OCH(CH₃)CN | — | Cl | OCH₃ | CH₃ | oil |
| 42 | OCH₃ | 6-Cl | Cl | CH₃ | CH₃ | m.p. 164–170° |
| 43 | OCH₃ | 6-Cl | Cl | OCH₃ | CH₃ | m.p. 91–94° |
| 44 | OCH₃ | 4-Cl | Cl | CH₃ | CH₃ | m.p. 177–178° |
| 45 | OCH₃ | 4-Cl | Cl | OCH₃ | CH₃ | m.p. 117–118° |
| 46 | OCH₃ | 4-Cl | Cl | OC₄H₉n | CH₃ | m.p. 137–138° |
| 47 | OCH(CH₃)CN | 4-Cl | Cl | CH₃ | CH₃ | vitreous |
| 48 | OCH(CH₃)CN | 4-Cl | Cl | OCH₃ | CH₃ | vitreous |
| 49 | OCH(CH₃)CN | 6-Cl | Cl | CH₃ | CH₃ | oil |
| 50 | OCH(CH₃)CN | 6-Cl | Cl | OCH₃ | CH₃ | oil |
| 51 | OCH₃ | 4,6-Cl₂ | Cl | CH₃ | CH₃ | m.p. 193–195° |
| 52 | OCH₃ | 4,6-Cl₂ | Cl | OCH₃ | CH₃ | m.p. 139–141° |
| 53 | OCH₃ | — | CF₃ | CH₃ | CH₃ | m.p. 104–106° |
| 54 | OCH₃ | — | CF₃ | OCH₃ | CH₃ | m.p. 78–79° |
| 55 | OCH₃ | 4-Cl | CF₃ | CH₃ | CH₃ | m.p. 121–125° |
| 56 | OCH₃ | 4-Cl | CF₃ | OCH₃ | CH₃ | $n_D^{25}$ 1.5500 |
| 57 | OCH₃ | 6-Cl | CF₃ | CH₃ | CH₃ | m.p. 157–161° |
| 58 | OCH₃ | 6-Cl | CF₃ | OCH₃ | CH₃ | m.p. 109–111° |
| 59 | OCH(CH₃)COOCH₃ | 4-Cl | Cl | CH₃ | CH₃ | m.p. 136–137° |
| 60 | OCH(CH₃)COOCH₃ | 4-Cl | Cl | OCH₃ | CH₃ | m.p. 82–86° |
| 61 | OCH(CH₃)COOCH₃ | 4-Cl | Cl | OC₄H₉n | CH₃ | m.p. 84–88° |
| 62 | OCH₃ | — | — | CH₃ | H | |
| 63 | OCH₃ | — | — | CH(CH₃)C≡CH | CH₃ | m.p. 175–176° |
| 64 | OCH₃ | — | — | (N-heterocycle with CH₃) | | m.p. 128–129° |
| 65 | OCH₃ | — | — | C₄H₉n | CH₃ | m.p. 71–72° |
| 66 | OCH₃ | — | — | C₂H₅ | CH₃ | m.p. 93–94° |
| 67 | OCH₃ | — | — | C₃H₇iso | CH₃ | m.p. 157–158° |
| 68 | OCOCH₂Cl | — | — | CH₃ | CH₃ | m.p. 84–85° |
| 69 | OCOCH₂Cl | — | — | OCH₃ | CH₃ | oil |
| 70 | OCOCHCl₂ | — | — | CH₃ | CH₃ | m.p. 82–83° |

-continued

| No. | OR₁ | R₂ | R₃ | R₄ | R₅ | Phys. data |
|---|---|---|---|---|---|---|
| 71 | OCOCHCl₂ | — | — | OCH₃ | CH₃ | oil |
| 72 | O-⟨C₆H₃⟩-CF₃ | — | — | CH₃ | CH₃ | |
| 73 | O-⟨C₆H₃⟩-CF₃ | — | — | OCH₃ | CH₃ | |
| 74 | OCONH-⟨C₆H₄⟩-CH₃ | — | — | CH₃ | CH₃ | m.p. 83–84° |
| 75 | OCONH-⟨C₆H₄⟩-CH₃ | — | — | OCH₃ | CH₃ | wax |
| 76 | OCONHCH₃ | — | — | CH₃ | CH₃ | m.p. 135–139° |
| 77 | OCONHCH₃ | — | — | OCH₃ | CH₃ | m.p. 123–126° |
| 78 | OCH₂CH=CH₂ | — | — | CH₃ | CH₃ | m.p. 83–85° |
| 79 | OCH₂CH=CH₂ | — | — | OCH₃ | CH₃ | m.p. 47–51° |
| 80 | OCONH-⟨C₆H₄⟩-CF₃ | — | — | CH₃ | CH₃ | m.p. 124–125° |
| 81 | OCONH-⟨C₆H₄⟩-CF₃ | — | — | OCH₃ | CH₃ | m.p. 192–194° |
| 82 | OC₄H₉n | — | — | CH₃ | CH₃ | m.p. 87–90° |
| 83 | OC₄H₉n | — | — | OCH₃ | CH₃ | oil |
| 84 | OCH₂CH=CHClCH₃ | — | — | CH₃ | CH₃ | |
| 85 | OCH₂CH=CHClCH₃ | — | — | OCH₃ | CH₃ | |
| 86 | OCH₂CCl=CH₂ | — | — | CH₃ | CH₃ | |
| 87 | OCH₂CCl=CH₂ | — | — | OCH₃ | CH₃ | |
| 88 | OCH₂C≡CH | — | — | CH₃ | CH₃ | m.p. 110–116° |
| 89 | OCH₂C≡CH | — | — | OCH₃ | CH₃ | oil |
| 90 | OCH(CH₃)COOCH₃ | — | — | CH₃ | CH₃ | m.p. 102–105° |
| 91 | OCH(CH₃)COOCH₃ | — | — | OCH₃ | CH₃ | oil |
| 92 | OCOCF₃ | — | — | CH₃ | CH₃ | m.p. 85–87° |
| 93 | OCOCF₃ | — | — | OCH₃ | CH₃ | m.p. 114–115° |
| 94 | OCH₂-⟨C₆H₄⟩-Cl | — | — | CH₃ | CH₃ | m.p. 85–87° |
| 95 | OCH₂-⟨C₆H₄⟩-Cl | — | — | OCH₃ | CH₃ | m.p. 95–96° |
| 96 | OCH₂-⟨C₆H₄⟩-Cl | — | — | CH₃ | CH₃ | |
| 97 | OCH₂-⟨C₆H₄⟩-Cl | — | — | OCH₃ | CH₃ | |
| 98 | OSO₂CH₃ | — | — | CH₃ | CH₃ | m.p. 101–103° |
| 99 | OSO₂CH₃ | — | — | OCH₃ | CH₃ | m.p. 64–68° |
| 100 | OCONHC₂H₄Cl | — | — | CH₃ | CH₃ | m.p. 100–110° |
| 101 | OCONHC₂H₄Cl | — | — | OCH₃ | CH₃ | oil |
| 102 | OCH₃ | — | — | (CH₂CH=CH₂)₂ | | m.p. 88–89° |
| 103 | OCH₃ | — | — | CHO | CH₃ | oil |
| 104 | OCH(CH₃)CH₂OH | 4-Cl | Cl | OCH₃ | CH₃ | m.p. 97–100° |
| 105 | OCH₃ | — | CN | CH₃ | CH₃ | m.p. 103–105° |
| 106 | OCH₃ | — | CN | OCH₃ | CH₃ | m.p. 104–105° |
| 107 | OCONHC₄H₉t. | — | — | C₄H₉t. | H | m.p. 65–67° |
| 108 | OCH(CH₃CSNH₂ | — | — | CH₃ | CH₃ | |
| 109 | OCH(CH₃)CSNH₂ | — | — | OCH₃ | CH₃ | |

| No. | OR₁ | R₂ | X | R₃ | R₄ | R₅ | Phys. data |
|---|---|---|---|---|---|---|---|
| 110 | OCH(CH₃)CSN=CHN(CH₃)₂ | — | — | | CH₃ | CH₃ | |
| 111 | OCH(CH₃)CSN=CHN(CH₃)₂ | — | — | | OCH₃ | CH₃ | |

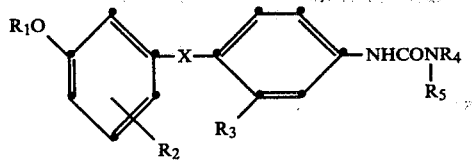

| No. | OR₁ | R₂ | X | R₃ | R₄ | R₅ | Phys. data |
|---|---|---|---|---|---|---|---|
| 112 | OCH₃ | | — S | | — CH₃ | CH₃ | m.p. 128–129° |
| 113 | OCH₃ | | — S | | — OCH₃ | CH₃ | m.p. 79–81° |
| 114 | OCH₃ | | — SO₂ | | — CH₃ | CH₃ | m.p. 129–140° |
| 115 | OCH₃ | | — SO₂ | | — OCH₃ | CH₃ | m.p. 120–121° |

EXAMPLE 3

The processing of the compounds of the formula I into compositions usable in agriculture can be carried out for example according to the following instructions.

Wettable Powder

The following constituents are used to produce
(a) a 70% wettable powder and (b) a 10% wettable powder:

(a)
70 parts of N-[4-(3'-methoxyphenoxy)-phenyl]-N',N'-dimethylurea,
5 parts of sodium dibutyl-naphthalene sulfonate,
3 parts of naphthalenesulfonic acid/phenolsulfonic acid/formaldehyde condensate (3:2:1),
10 parts of kaolin, and
12 parts of Champagne chalk; and (b)
10 parts of active substance,
3 parts of a mixture of the sodium salts of saturated fatty alcohol sulfates,
5 parts of naphthalenesulfonic acid/formaldehyde condensate, and
82 parts of kaolin.

The given active substance is absorbed onto the appropriate carriers (kaolin and chalk), and the material is subsequently mixed and ground with the remaining constituents. Wettable powders having excellent wetting and suspension properties are obtained. It is possible to obtain from wettable powders of this type, by dilution with water, suspensions containing 0.1 to 8% of active substance, these suspensions being suitable for combating weeds in crops of cultivated plants.

Emulsion Concentrate

The following constituents are mixed together to produce a 25% emulsion concentrate:
25 parts of N-[4-(3'-methoxyphenoxy)-phenyl]-N'-methyl-N'-methoxyurea,
10 parts of a mixture of nonylphenolpolyoxyethylene and calcium dodecylbenzene sulfonate,
10 parts of cyclohexanone, and
55 parts of xylene.

This concentrate can be diluted with water to give emulsions of suitable concentration, for example 0.1%, and these emulsions are suitable for combating weeds in crops of cultivated plants.

Paste

The following materials are used to produce a 45% paste:
45 parts of N-[4-(3'-methoxyphenoxy)-phenyl]-N',N'-dimethylurea,
5 parts of sodium aluminium silicate,
14 parts of cetyl polyglycol ether having 8 mols of ethylene oxide,
1 part of oleyl polyglycol ether having 5 mols of ethylene oxide,
2 parts of spindle oil,
10 parts of polyethylene glycol, and
23 parts of water;

(b)
45 parts of N-[4-(3'-methoxyphenoxy)-phenyl]-N'-methyl-N'-methoxyurea,
5 parts of ethylene glycol,
3 parts of octylphenoxypolyethylene glycol having 9–10 mols of ethylene oxide per mol of octylphenol,
3 parts of a mixture of aromatic sulfonesulfonic acids condensed with formaldehyde as ammonium salt,
1 part of silicone oil in the form of a 75% emulsion,
0.1 part of a mixture of 1-(3-chloroallyl)-3,5,7-triazonium-adamantane chloride with sodium carbonate, chloride value at least 11.5%,
0.2 part of a bipolymeric thickener having a maximum of 100 nuclei per gram, and
42.7 parts of water.

The active substance is intimately mixed and ground with the additives in suitable apparatus. There is obtained a paste from which suspensions of the desired concentration can be produced by dilution with water.

EXAMPLE 4

The herbicidal activity of the compounds of the formula I has been established by the following tests.

Pre-emergence Herbicidal Action (Inhibition of Germination)

Plant seeds are sown in flower pots of 12–15 cm diameter in a greenhouse, and immediately afterwards the surface of the soil is treated with an aqueous dispersion of the active substance, obtained from an emulsion concentrate, flowable, or wettable powder. Various concentration series are used, and the amount of active substance applied is expressed in kg per hectare. The pots are then kept in a greenhouse at a temperature of 22°–25° with 50–70% relative humidity, and the test is evaluated after 3 weeks.

The compounds 1-8 exhibited in applied amounts of less than 1 kg/hectare a good herbicidal action in this test.

Post-emergence Herbicidal Action (Contact Herbicide)

A considerable number of weeds and cultivated plants, both monocotyledonous and dicotyledonous, are sprayed after emergence (in the 4- to 6-leaf stage) with an aqueous active-substance dispersion in dosages per hectare of 2 and 1 kg, respectively, of active substance, and the weeds and plants are then kept at 24°-26° with 45-60% relative humidity. The test is evaluated 15 days after the treatment, and the results are assessed on the basis of the following scale of ratings (EWRC valuation) [European Weed Research Council].
1 = plants have not germinated or have fully died off,
2-3 = very intense action,
4-6 = moderate action,
7-8 = slight action,
9 = no action (as in the case of untreated control plants),
— = plant not tested.
The results are summarised in the following Table.

| Plant | Compound No. | | | | | | | | | | | | | | | |
|---|---|---|---|---|---|---|---|---|---|---|---|---|---|---|---|---|
| | 1 | | 17 | | 18 | | 34 | | 39 | | 53 | | 56 | | 113 | |
| | Applied amount in kg/hectare | | | | | | | | | | | | | | | |
| | 2 | 1 | 2 | 1 | 2 | 1 | 2 | 1 | 2 | 1 | 2 | 1 | 2 | 1 | 2 | 1 |
| barley | 5 | 9 | — | — | 7 | 9 | 8 | 8 | 4 | 5 | — | — | — | — | 7 | 9 |
| wheat | 4 | 9 | 9 | 9 | 7 | 9 | 8 | 9 | 9 | 9 | 9 | 9 | 7 | 8 | 8 | 9 |
| abutilon sp. | 1 | 1 | 1 | 1 | 1 | 1 | 1 | 1 | 1 | 1 | 1 | 1 | 1 | 1 | 1 | 1 |
| sida spinosa | 1 | 1 | — | — | 4 | 6 | 5 | 5 | 1 | 1 | — | — | — | — | 1 | 2 |
| xanthium | — | — | 1 | 2 | 1 | 1 | — | — | — | — | 1 | 1 | 1 | 1 | 4 | 7 |
| amarantus retroflexus | 1 | 1 | — | — | 1 | 2 | 1 | 2 | 1 | 1 | — | — | — | — | 1 | 1 |
| chenopodium album | 1 | 2 | 1 | 3 | 1 | 1 | — | — | — | — | 1 | 1 | 1 | 1 | 1 | 2 |
| solanum nigrum | 1 | 1 | — | — | 2 | 2 | 1 | 2 | 1 | 1 | — | — | — | — | 1 | 1 |
| ipomoea purp. | 1 | 2 | 2 | 3 | 1 | 1 | 2 | 3 | 1 | 1 | 1 | 3 | 2 | 3 | 3 | 4 |
| sinapis alba | 1 | 1 | 1 | 1 | 1 | 1 | 1 | 1 | 1 | 1 | 1 | 2 | 1 | 2 | 1 | 4 |
| stellaria media | 1 | 2 | — | — | 1 | 1 | 2 | 4 | 1 | 1 | — | — | — | — | 1 | 2 |
| galium aparine | 1 | 2 | 1 | 1 | 1 | 1 | 3 | 4 | 1 | 2 | 5 | 5 | 4 | 5 | 3 | 4 |
| viola tricolor | 2 | 2 | 1 | 1 | 1 | 2 | — | — | — | — | 2 | 3 | 2 | 3 | 2 | 2 |
| veronica | 1 | 1 | — | — | 1 | 1 | — | — | — | — | — | — | — | — | 1 | 1 |
| kochi | — | — | — | — | — | — | 3 | 3 | 1 | 1 | — | — | — | — | — | — |
| portulacca | 1 | 1 | — | — | — | — | 1 | 2 | 1 | 1 | — | — | — | — | — | — |
| sesbania exaltata | 1 | 2 | — | — | — | — | 1 | 1 | 1 | 1 | — | — | — | — | — | — |

Selective Herbicidal Action on Soya-bean Plants

The test plants are sown in sterilised soil in flower pots in a greenhouse. When the plants have reached the 4-6-leaf stage, the active substance is applied as an aqueous emulsion to the plants in such a manner that the amount applied corresponds to 1 kg of active substance per hectare in the field. The pots are then put into an air-conditioned greenhouse at 22°-25° with 60-70% relative humidity and are watered every day. Checking and assessment of growth are carried out after 3 weeks and the condition of the plants is evaluated according to the scale of ratings given in the foregoing.

The results with an applied amount of 1 kg/hectare are as follows:

| | Compound No. | | | | | | | | |
|---|---|---|---|---|---|---|---|---|---|
| | 1 | 2 | 7 | 8 | 18 | 26 | 40 | 45 | 48 |
| Plant | | | | | | | | | |
| soya-bean | 7 | 9 | 7 | 7 | 6 | 6 | 6 | 8 | 8 |
| digitaria sanguinalis | 1 | 4 | 9 | 9 | 2 | 3 | 2 | 6 | 9 |
| sida spinosa | 1 | 4 | 6 | 6 | 6 | 9 | 4 | 4 | 3 |
| amarantus retroflexus | 1 | 1 | 2 | 2 | 2 | 2 | 2 | 2 | 4 |
| iopomoea purpurea | 1 | 4 | 2 | 2 | 1 | 3 | 3 | 5 | 6 |

| | Compound No. | | | | | | | |
|---|---|---|---|---|---|---|---|---|
| | 1 | 2 | 7 | 8 | 18 | 26 | 40 | 45 | 48 |
| abutilon sp. | 1 | 3 | 2 | 2 | 1 | 1 | 7 | 7 | 1 |

Selective Herbicidal Action on Rice in the Post-emergence Process

Rice plants which are 25 days old are transplanted in a greenhouse into rectangular eternit trays. Between the rows of rice plants there are then sown seeds of the weeds occurring in rice crops, namely, *Echinochloa crus galli, Cyperus difformis, Ammania indica* and *Rotala indica*. The trays are well watered and are kept at a temperature of about 25° with high relative humidity. After 12 days, when the weeds have emerged and have reached the 2-3-leaf stage, the soil in the tray is covered with a 2.5 cm deep layer of water. The active substance is then applied as an emulsion concentrate, by means of pipette, between the rows of plants, the emulsion concentrate being diluted to the extent that it corresponds to an applied amount in the field of 4 and 2 kg of active substance per hectare. The test is evaluated after 4 weeks, and the condition of the plants is assessed on the basis of the scale of ratings given in the foregoing. The results obtained are as follows:

| Applied amount in kg/hectare | Plant | | | | | | | | | |
|---|---|---|---|---|---|---|---|---|---|---|
| | Rice | | echinochloa crus galli | | cyperus difformis | | ammania indica | | rotala indica | |
| | 4 | 2 | 4 | 2 | 4 | 2 | 4 | 2 | 4 | 2 |
| Compound No. | | | | | | | | | | |
| 2 | 4 | 6 | 1 | 1 | 1 | 1 | 1 | 1 | 1 | 1 |
| 3 | 9 | 9 | 2 | 3 | 1 | 2 | 2 | 2 | 7 | 8 |
| 5 | 6 | 7 | 2 | 6 | 2 | 3 | 1 | 2 | 1 | 2 |
| 18 | 9 | 9 | 7 | 8 | 1 | 4 | 1 | 2 | 6 | 7 |
| 39 | 4 | 7 | 2 | 6 | 1 | 1 | 1 | 1 | 2 | 2 |
| 41 | 8 | 9 | 4 | 8 | 1 | 2 | 1 | 1 | 1 | 1 |
| 45 | 8 | 9 | 1 | 3 | 3 | 3 | 1 | 1 | 1 | 1 |

Desiccation and Defoliation Action

Cotton plants of the Deltapine variety are grown in clay pots in a greenhouse. After the bolls have finished forming, the plants are sprayed with aqueous preparations of the active substance No. 1 in amounts corresponding to 1.2, 0.6 and 0.3 kg per hectare in the field. Untreated plants are used as control specimens. An evaluation of the test is made 3, 7 and 14 days after application of the test substance by determining the degree of defoliation (% of leaves which have fallen) and of desiccation (% drying out of the leaves remaining on the plant).

In this test, the compounds 1, 17, 18 and 113 in applied amount of 0.6 and 1.2 kg/hectare, respectively, left after 7 days just a very few dried up leaves on the plants (>80% leaf-fall and desiccation).

What is claimed is:

1. A compound of the formula

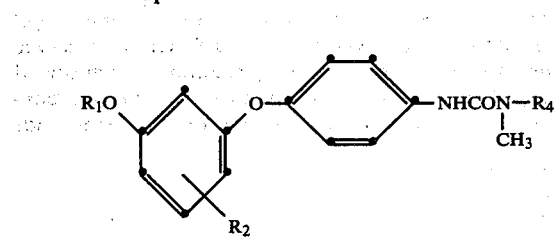

wherein
$R_1$ is a straight-chain or branched-chain $C_1$–$C_6$-alkyl group,
$R_2$ is hydrogen, halogen, methyl or methoxy, and
$R_4$ is methyl or methoxy.

2. A compound according to claim 1 of the formula

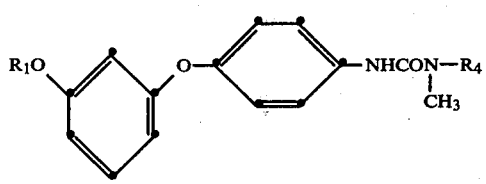

3. The compound according to claim 2 which is N-[4-(3'-methoxyphenoxy)-phenyl]-N',N'-dimethylurea.

4. The compound according to claim 2 which is N-[4-(3'-methoxyphenoxy)-phenyl]-N'-methyl-N'-methoxyurea.

5. The compound N-[3-chloro-4-(3'-methoxyphenoxy)-phenyl]-N',N'-dimethylurea.

6. The compound N-[3-chloro-4-(3'-methoxyphenoxy)-phenyl]-N'-methyl-N'-methoxyurea.

7. The compound according to claim 1 which is N-[4-(3',5'-dimethoxyphenoxy)-phenyl]-N',N'-dimethylurea.

8. The compound according to claim 1 which is N-[4-(3',5'-dimethoxyphenoxy)-phenyl]-N'-methyl-N'-methoxyurea.

9. The compound according to claim 1 which is N-[4-(3'-methoxy-6'-chlorophenoxy)-phenyl]-N',N'-dimethylurea.

10. The compound N-[4-(3'-propargyloxyphenoxy)-phenyl]-N',N'-dimethylurea.

11. The compound N-[4-(3'-propargyloxyphenoxy)-phenyl]-N'-methyl-N'-methoxyurea.

12. The compound according to claim 2 which is N-[4-(3'-ethoxyphenoxy)-phenyl]-N'-methyl-N'-methoxyurea.

13. The compound according to claim 2 which is N-[4-(3'-ethoxyphenoxy)-phenyl]-N',N'-dimethylurea.

14. A herbicidal composition which contains as active ingredient a herbicidally effective amount of a urea compound of claim 1, 5, 6, 10 or 11, together with inert additivies.

15. A method for selectively combatting undesirable plant growth in cultivated crops of wheat, which comprises applying to the locus of said crops a herbicidally effective amount of a urea compound of claim 1, 5, 6, 10 or 11.

16. A method for selectively combatting undesirable plant growth in cultivated crops of wheat, which comprises applying to the locus of said crops a herbicidally effective amount of the urea compound of claim 3.

17. A method for selectively combatting undesirable plant growth in cultivated crops of wheat, which comprises applying to the locus of said crops a herbicidally effective amount of the urea compound of claim 4.

* * * * *